United States Patent [19]

Fernley et al.

[11] Patent Number: 4,891,155

[45] Date of Patent: Jan. 2, 1990

[54] PREPARATION OF ALKYL ARYL SULFONATE CONCENTRATES HAVING LOW VISCOSITY

[75] Inventors: George W. Fernley; Gerdina J. R. Daane-Pluim; Hendrik T. Verkouw, all of Amsterdam, Netherlands

[73] Assignee: Shell Oil Company, Houston, Tex.

[21] Appl. No.: 803,708

[22] Filed: Dec. 2, 1985

Related U.S. Application Data

[63] Continuation of Ser. No. 596,973, Apr. 5, 1984, abandoned.

[30] Foreign Application Priority Data

Apr. 8, 1983 [GB] United Kingdom ............... 8309632

[51] Int. Cl.$^4$ ................... B01F 17/00; B01F 17/30; C07C 143/24; E21B 43/16
[52] U.S. Cl. ................... 252/354; 252/353; 252/8.554; 166/275; 562/97
[58] Field of Search ............ 260/505 N; 252/558, 252/559, 553, 556, 353, 354

[56] References Cited

U.S. PATENT DOCUMENTS

| | | | |
|---|---|---|---|
| 2,325,320 | 7/1943 | Holuba | 260/505 N |
| 2,673,207 | 3/1954 | Trusler | 260/505 N |
| 4,061,586 | 12/1977 | Klisch et al. | 252/556 |

Primary Examiner—A. Lionel Clingman
Assistant Examiner—John F. McNally

[57] ABSTRACT

The invention relates to alkyl aryl sulfonate concentrate compositions and provides a process wherein an aqueous solution containing at least 10% by weight of a neutralizing agent is mixed with at least one $C_{2-9}$ saturated alcohol and with a $C_{8-18}$ alkyl aryl (xylene or toluene) sulfonic acid, the relative quantities of the components being such that the resulting neutralized mixture contains 5 to 40 parts by weight of the alcohol per 100 parts by weight of alkyl aryl sulfonate salt. The resulting flowable liquid concentrate composition are easily handled materials having application, for instance, in enhanced oil recovery processes.

20 Claims, No Drawings

PREPARATION OF ALKYL ARYL SULFONATE CONCENTRATES HAVING LOW VISCOSITY

This is a continuation of application Ser. No. 596,973, filed Apr. 5, 1984, now abandoned.

BACKGROUND OF THE INVENTION

This invention relates to a process for the preparation of alkyl aryl sulfonate compositions, and more particularly to the preparation of concentrated sulfonate compositions of low viscosity.

Alkyl aryl sulfonates are known materials, recognized for their valuable solvent and surface active properties in a variety of applications. As an example, they have been recommended for use in various detergent formulations. Moreover, because of chemical and thermal stability, they have proved to be particularly attractive for use in various enhanced oil recovery processes. U.S. Pat. Nos. 3,799,263, 3,861,466, 4,022,699 and the commonly-assigned, copending application Ser. No. 560,468, filed Dec. 12, 1983, for instance, describe the use of alkyl xylene sulfonates in oil recovery services.

One drawback to the conventional use of alkyl aryl sulfonates in all such applications is the high viscosity which has been characteristic of the sulfonates in concentrated form. The sulfonates of interest are conventionally prepared by reacting one or more alkyl aryl hydrocarbons with, for example, sulfur trioxide or fuming sulfuric acid to first produce alkyl aryl sulfonic acid. When these acids are then neutralized to yield the sulfonate salts, the thick, paste-like consistency of the product gives rise to problems in transportation, storage, and formulation.

It is known to be possible to dilute the sulfonate salts thus produced to lower their viscosity and improve their handling characteristics. However, this has entailed the inclusion in the product of a substantial amount of a diluent. The need for diluent often represents an added material cost. Moreover, and often more importantly, there is an added cost associated with transporting and storing the larger quantities of diluted sulfonate mixture. These factors are of particular significance when the alkyl aryl sulfonates are applied to oil recovery service. In many cases, the remote location of the oil production site increases the difficulty and expense of transportation and storage. Although the sulfonates are necessarily diluted before use, suitable diluents (e.g., brine and oil) are readily available at, and need not be transported to, the production site. In fact, the recovery process typically call for the injection into the oil-bearing formation of a dilute (e.g., 1% by weight) solution of alkyl aryl sulfonate in brine, or for the injection of a sulfonate and oil mixture into a reservoir prior to water-flooding.

Accordingly, it is a principal object of this invention to provide a method for preparing alkyl aryl sulfonate compositions of low viscosity. It is a further object to accomplish this in a way which maintains the products as concentrates and which, in particular, does not depend upon the inclusion of large proportions of oils, water or other diluents.

In part, the present invention accomplishes these objects by incorporating a lower aliphatic alcohol into the desired sulfonate product at a critical stage of sulfonate preparation. There are teachings in the prior art of alkyl aryl sulfonate compositions containing lower aliphatic alcohols. For instance, L. W. Holm in the aforementioned U.S. Pat. No. 4,022,699, U.S. Pat. No. 3,769,209, and also in Canadian Pat. No. 1,011,215 discloses alkyl aryl sulfonate compositions containing alcohols which act as stabilizing agents, rendering the sulfonate more effective and enhancing the properties of microemulsions formed from the compositions during oil recovery applications. However, no criticality is suggested by these patents for the order of processing steps utilizing in the preparation of the alkyl aryl sulfonates. Moreover, the compositions described in these patents contain substantial amounts of oils which act as diluents for the sulfonate concentrates.

SUMMARY OF THE INVENTION

The present invention provides an improved process for the preparation of low-viscosity alkyl aryl sulfonate concentrates. in general terms, the invention entails the neutralization of alkyl aryl sulfonic acids to alkyl aryl sulfonates and the preparation of sulfonate concentrates having limited contents of a lower saturated alcohol and water. In one respect, the invention can be expressed as an improvement over conventional processes for the preparation of such neutralized sulfonate concentrates. This improvement centers upon neutralization of the alkyl aryl sulfonic acid by simultaneous contact with both a neutralizing agent and a lower saturated alcohol having a carbon number in the range from 2 to 9. For purposes of the invention, critical restrictions are necessarily placed upon the relative proportions of the components and upon the minimum content of alkyl aryl sulfonates in the resulting neutralized concentrate.

In a particularly preferred embodiment, the invention can be expressed as a two step neutralization of the alkyl aryl sulfonic acid. According to this embodiment, the invention comprises as a first step the mixing of the alcohol and the aqueous neutralizing agent and as a second step the mixing of the mixture resulting from the first step with the alkyl aryl sulfonic acid.

It is surprisingly found that by incorporating the alcohol and water into the sulfonate at the time of neutralization, there is prepared a concentrate product having the desired improvement in viscosity and handling properties.

DETAILED DESCRIPTION OF THE INVENTION

The invention is particularly applicable to the preparation of sulfonate concentrates from alkyl aryl sulfonic acids of the formula

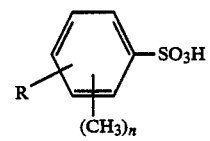

where n is 1 or 2 and R is a $C_8$ to $C_{18}$ alkyl group. R is more preferably a $C_8$ to $C_{16}$ alkyl group, most preferably a $C_{11}$ to $C_{16}$ alkyl group. It is to be understood that these preferences relate largely to considerations of utility of the desired alkyl aryl sulfonate. In enhanced oil recovery, for instance, the choice of an optimal alkyl aryl sulfonate for any given application will depend upon such factors as the salinity level in the particular oil-bearing formation. Sulfonic acids of the above formula are well known in the art as the reaction products of the corresponding alkyl aryl hydrocarbons with sulfonating agents such as sulfur trioxide and fuming sulfuric acid.

In all cases of interest, the sulfonic acids are neutralized to the sulfonate salts. For this purpose, the sulfonic acids are contacted with a base, preferably ammonium hydroxide or an alkali metal hydroxide. The alkali metal hydroxides are particularly preferred for use as neutralizing agents, and sodium hydroxide is considered most preferred.

It is necessary to the present invention that neutralization of the alkyl aryl sulfonic acid be conducted using an aqueous solution of the neutralizing agent. The aqueous solution contains at least about 10%w (percent by weight) of neutralizing agent. Concentrations of at least about 20%w are preferred, while concentrations of at least about 30%w are more preferred and concentrations of at least about 40%w are considered most preferred. If desired, a saturated solution of the neutralizing agent may be employed. Sulfonic acid is mixed with that quantity of the aqueous solution of the neutralizing agent which is necessary to bring the mixture to about neutral pH. Excess neutralizing agent may be added if desired.

It is further necessary to the invention that contact between the alkyl aryl sulfonic acid and the neutralizing agent take place in the presence of at least one saturated alcohol having a carbon number in the range from 2 to 9, inclusive, preferably in the range from 3 to 9, inclusive. Examples of individual alcohols suitable for this purpose include ethanol, isopropanol, s-butanol, n-butanol, isobutanol, t-butanol, t-amyl alcohol, methyl isobutyl carbinol, and 2-ethylhexanol. Mixtures of $C_2$ to $C_9$ saturated alcohols are very suitable. The butanols, and particularly s-butanol, are most preferred when the intended use of concentrate is in oil recovery service. In general, the amount of alcohol employed should be between about 5 and 40 parts by weight for every 100 parts by weight of alkyl aryl sulfonate. Although the optimal quanity of alcohol relative to sulfonate salt will be expected to very with different alkyl aryl sulfonates and different carbon numbers of the alcohol, a preference may typically be expressed for an amount of alcohol that is between about 10 and 30 parts by weight for each 100 parts by weight of the sulfonate.

In neutralizing the alkyl aryl sulfonic acid for purposes of the invention, provision is made in the course of mixing with aqueous neutralizing agent solution and alcohol to produce a product containing at least about 53%w, preferably at least about 60%w, most preferably at least about 65%w, of the neutralized alkyl aryl sulfonate salt. Typically, the process yields a concentrate containing between about 53 and 89%w of the alkyl aryl sulfonate salt and between about 2.65 and 27%w alcohol, with the balance being water and minor amounts of incidental components.

The preparation of alkyl aryl sulfonate concentrate of low viscosity requires essentially simultaneous contact of the sulfonic acid with both the alcohol and the aqueous solution of neutralizing agent. If the sulfonic acid is first thoroughly contacted with only the neutralizing agent, the neutralized sulfonate does not have the desired low viscosity. Subsequent addition of alcohol, in such proportions as are used in the invention, does not readily convert the viscous sulfonate to the desired mobile liquid. Contact of the sulfonic acid with the alcohol alone is also unacceptable, with the acid typically acting to cause side reactions, particularly the dehydration of the alcohol to olefin.

Simultaneous contact of the three components is most readily accomplished by first preparing a mixture of the alcohol and aqueous neutralizing agent solution, and then contacting and mixing the resulting mixture with the alkyl aryl sulfonic acid. Each step of such a two step process may be carried out either batchwise or continuously. In order to minimize exposure of the alcohol component to unneutralized acid in a second mixing step operated in a batch mode, the alkyl aryl sulfonic acid should be added to the aqueous alcohol and neutralizing agent mixture, or the acid and the mixture should be simultaneously streamed into a mixing vessel.

Neutralization of the sulfonic acids, in the presence of the alcohol, may be effected over a wide range of temperatures, for instance, temperatures between about 10° C. and 80° C.

In accordance with a preferred embodiment of the invention, the process further includes a step for blending the resulting sulfonate salt concentrate with up to 100 parts by weight, more preferably between 5 and 40 parts by weight (per 100 parts by weight of the alkyl aryl sulfonate salt) of a cosurfactant, selected from one or more anionic or nonionic surfactants, particularly one or more surfactants selected from the group consisting of alcohol ethoxysulfates, alcohol ethoxylates, alcohol ethoxyacetates, alcohol ethoxysulfonates alpha-olefin sulfonates, and mixtures thereof. Preferably the cosurfactant is one or more alcohol ethoxysulfates or one or more alpha-olefin sulfonates. The cosurfactant preferably has an average molecular weight in the range from about 300 to 750, more preferably in the range from about 370 to 450.

The invention is further illustrated by reference to the following Examples representing practice in accordance with the invention, and Comparative Examples, representing practice not in accordance with the invention.

EXAMPLE 1

A composition was prepared by mixing 18 parts by weight of s-butanol and a sufficient quantity of an aqueous solution of sodium hydroxide (sodium hydroxide concentration of 46%w) to neutralize 100 parts by weight of an alkyl aryl sulfonic acid blend. The blend contained 87%w sulfonic acids which were alkyl-o-xylene sulfonic acids having an average equivalent weight of 400 and having alkyl groups (R in formula I) of between 11 and 16 carbon atoms. To the resulting s-butanol/hydroxide mixture at ambient temperature (20°) was added with stirring 100 parts by weight of the alkyl-o-xylene sulfonic acid. The resulting concentrate was a clear, golden, mobile liquid. Composition and viscosity of the concentrate is summarized in Table I, below.

COMPARATIVE EXAMPLE A

An attempt was made to prepare a concentrate similar to that produced in Example 1 by taking 100 parts by weight of the alkyl-o-xylene sulfonic acid blend, adding 20 parts by weight of s-butanol and subsequently neutralizing with 46%w aqueous sodium hydroxide. The attempt failed. The acid dehydrated the s-butanol to butene.

COMPARATIVE EXAMPLE B 100 parts by weight of the alkyl-o-xylene sulfonic acid used in Example 1 was neutralized with 46%w aqueous sodium hydroxide. To the resulting thick paste was added 20 parts by weight s-butanol. On simple stirring the mixture remained a thick, difficult to handle, paste. On heating to 70° C. and after continued and prolonged vigorous stirring at that temperature the mixture became clear and mobile, and on cooling to ambient temperature remained a clear, golden, mobile liquid similar in appearance to the composition of Example 1.

EXAMPLE 2

The procedures of Example 1 were followed, except that an aqueous solution of sodium hydroxide having a concentration of 24%w sodium hydroxide was used to prepare the aqueous hydroxide/butanol mixture. Composition and viscosity of the resulting concentrate are summarized in Table I.

EXAMPLE 3

To 94 parts by weight of an alkyl aryl sulfonate concentrate prepared as described in Example 1, was added 6 parts by weight of an alcohol ethoxysulfate cosurfactant ("DOBANOL 25-35/60"; DOBANOL is a registered trademark) containing 58 to 60% active matter of average molecular weight 441, derived from $C_{12}$–$C_{15}$ alcohols and containing an average of three ethylene oxide adducts per molecule. Composition and viscosity of the resulting concentrate are summarized in Table I.

COMPARATIVE EXAMPLE C

The procedure of Example 1 was again followed, using an aqueous sodium hydroxide solution having a concentration of 15%w. The resulting sulfonate had a concentration of only 48%w. Composition and viscosity are summarized in Table I.

TABLE I

| | Example | | | Comparative |
|---|---|---|---|---|
| | 1 | 2 | 3 | |
| % w alkyl xylene sulfonate, sodium salts (AXS) | 65 | 57 | 61 | 48 |
| % w s-butanol (parts per 100 parts AXS) | 13(20) | 11(19) | 12(20) | 10(21) |
| % w alcohol ethoxysulfate (parts per 100 parts AXS) | — | — | 6(10) | — |
| % w water (including minor amounts of incidental components) | 22 | 32 | 21 | 42 |
| Viscosity, m la.s at: 90 s$^{-1}$ | 1200 | 650 | 900 | * |
| 220 s$^{-1}$ | 1200 | 650 | 900 | * |
| 350 s$^{-1}$ | 1100 | 635 | 860 | * |
| 440 s$^{-1}$ | 1060 | 625 | 830 | * |

* not measurable; too viscous, non-homogeneous product.

EXAMPLES 4 TO 6

Further compositions were prepared following a similar procedure to that of Examples 1 and 2, using a similar alkyl-o-xylene sulfonic acid blend (containing 98%w pure acid) having average equivalent weight 400 and wherein the alkyl moiety contained 11 to 16 carbon atoms, and an aqueous sodium hydroxide solution of concentration 46%w, but employing different quantities of s-butanol. The compositions of the resulting concentrates, which were clear, golden, mobile liquids, are given in the following Table II together with their viscosities, measured at 40° C. using a "HAAKE ROTOVISCO" (trade mark) viscometer.

TABLE II

| | Example | | |
|---|---|---|---|
| | 4 | 5 | 6 |
| % w alkyl xylene sulfonate, sodium salt (AXS) | 75 | 72 | 70 |
| % w s-butanol (parts per 100 AXS) | 11(15) | 14(19) | 17(24) |
| % w water (including minor amounts of incidental components) | 14 | 14 | 13 |
| Viscosity, m Pa.s at: 100 s$^{-1}$ | 480 | 335 | 240 |
| 200 s$^{-1}$ | 480 | 340 | 240 |
| 300 s$^{-1}$ | 480 | 340 | 235 |
| 500 s$^{-1}$ | 470 | 335 | 225 |
| 700 s$^{-1}$ | 460 | 320 | 215 |

EXAMPLES 7 AND 8

In Example 7 a composition was prepared following a procedure similar to that of Examples 1 and 2, using an alkyl-o-xylene sulfonic acid blend similar to those used in Examples 1 to 6 except that it contained 96%w pure acid, and a sodium hydroxide solution of concentration 46%w.

In Example 8, 93 parts by weight of the composition prepared as described for Example 7 was further blended with 7 parts by weight of the alcohol ethoxysulfate described in Example 3.

The viscosities of the compositions, which were clear, golden, mobile liquids, were measured at 20° C. and 40° C. using a "HAAKE ROTOVISCO" (trade mark) viscometer, results being given in Table III following.

TABLE III

| | Example | |
|---|---|---|
| | 7 | 8 |
| % w alkyl xylene sulfonate, sodium salt (AXS) | 71 | 66 |
| % w s-butanol (parts per 100 parts AXS) | 14(20) | 13(20) |
| % w alcohol ethoxy sulfate (parts per 100 parts AXS) | — | 7(10) |
| % w water (including minor amounts of incidental components) | 15 | 14 |
| Viscosity, m Pa.s at: 20° C., 100 s$^{-1}$ | 1050 | 830 |
| 200 s$^{-1}$ | 1030 | 795 |
| 300 s$^{-1}$ | 920 | 785 |
| 40° C., 100 s$^{-1}$ | 280 | 205 |
| 200 s$^{-1}$ | 280 | 220 |
| 300 s$^{-1}$ | 275 | 215 |

EXAMPLE 9 TO 17

Following the procedures of Examples 3 and 8, using an alkyl-o-xylene sulfonic acid blend similar to those used in Examples 1 to 8 except that it contained 97% pure acid, a sodium hydroxide solution of concentration 46%w, the same alcohol ethoxysulfate, and a variety of different alcohols, there were prepared a number of concentrates of the following general composition:

| | |
|---|---|
| alkyl xylene sulfonate, sodium salt (AXS) | 57% w |
| alcohol (parts per 100 parts AXS) | 12% w (21) |
| alcohol ethoxy sulfate (parts per 100 parts AXS) | 18% w (32) |
| water (including minor amounts of incidental components | 13% w |

The compositions were all clear, golden, mobile liquids.

The alcohols used, together with viscosities of the resulting compositions, measured using a Ubbelohde viscometer at 20° C. and 40° C., are given in the following Table IV:

TABLE IV

| Example | Alcohol | Viscosity in mm$^2$/s | |
|---|---|---|---|
| | | 20° C. | 40° C. |
| 9 | isopropanol | 270 | 90 |
| 10 | s-butanol | 435 | 140 |
| 11 | n-butanol | 525 | 165 |
| 12 | isobutanol | 560 | 175 |
| 13 | t-butanol | 525 | 160 |
| 14 | t-amyl alcohol | 700 | 210 |
| 15 | methyl isobutyl carbinol | 945 | 260 |
| 16 | 2-ethylhexanol | 1715 | 450 |
| 17 | "LINEVOL 79" (registered trade mark) | 1665 | 455 |

("LINEVOL 79" is a mixture of $C_{7-9}$ primary alcohols, having a specific gravity of 0.832 at 20° C.)

The compositions of Examples 9 to 14 were subsequently stored at 10° C. and remained liquid indefinitely.

EXAMPLE 18

A composition was prepared according to the procedure of Example 8 using the same alkyl xylene sulfonic acid, s-butanol, a sodium hydroxide solution of concentration 46%w and the same alcohol ethoxy-sulfate. Samples of the resulting composition, which was a clear, golden, mobile liquid were diluted with progressively larger amounts of water and the physical state of the resulting mixtures was observed. Results are given in the following Table V, sample a being the undiluted composition.

TABLE V

| Sample | a | b | c | d | e | f | g | h | i |
|---|---|---|---|---|---|---|---|---|---|
| % w alkyl xylene sulfonate, sodium salt (AXS) | 66 | 63 | 55 | 47 | 40 | 32 | 24 | 16 | 8 |
| % w water | 14 | 17 | 28 | 38 | 48 | 59 | 68 | 79 | 89 |
| Physical state | mobile liquid | | | | very viscous liquid or gel | | | | mobile liquid |

COMPARATIVE EXAMPLE D

A commerical petroleum sulfonate product (containing 60%w) sulfonate salt of an average equivalent weight of 465, the balance being 14%w non-sulfonatable organic matter and 26%w water with a minor amount of sodium sulfate) was blended with "LINEVOL 79" (registered trade mark) and the alcohol ethoxysulfate used in Example 3. The blend contained 80%w of the commerical petroleum sulfonate product, 12%w of the LINEVOL alcohol and 8%w of the alcohol ethoxysulfate.

At ambient temperature, this blend was a thick, black material with viscosity characteristics (measured using a "FANN" (trademark)viscometer) shown in Table VI.

TABLE VI

| Temperature | Viscosity, m la.s at | |
|---|---|---|
| | 15 s$^{-1}$ | 1500 s$^{-1}$ |
| 20° C. | 9500 | 8000 |
| 45° C. | 1300 | 1250 |
| 70° C. | 350 | 340 |

EXAMPLE 19

A mixture was prepared from 34 parts by weight of s-butanol and 25 parts by weight of an aqueous solution of sodium hydroxide (sodium hydroxide concentration 46%w). To this s-butanol/hydroxide mixture at ambient temperature (20° C.) was added with stirring 100 parts by weight of an alkyl-o-xylene sulfonic acid blend (94.2%w pure acid). The sulfonic acids had an average equivalent weight of 348 and an alkyl moiety of 8–14 carbon atoms. 74 parts by weight of the resulting neutralized sulfonate concentrate (a clear, amber, mobile liquid) was then blended with 26 parts by weight of an alpha-olefin sulfonate cosurfactant containing 40% active matter of average molecular weight 310 derived from $C_{14}$–$C_{16}$ alpha-olefins. Composition and viscosity of final mixture is given in the following table VII. Viscosity was measured using a Ubbelohde viscometer.

TABLE VII

| | | |
|---|---|---|
| % w alkyl xylene sulfonate, sodium salts (AXS) | | 48 |
| % w s-butanol (parts per 100 parts AXS) | | 16 (33) |
| % w alpha-olefin sulfonate (parts per 100 parts AXS) | | 10 (21) |
| % w water (including minor amounts of incidental components) | | 26 |
| Viscosity in mm$^2$/s | 20° C. | 160 |
| | 40° C. | 56 |

What is claimed is:

1. In a process for preparing an alkyl aryl sulfonate concentrate which comprises neutralizing at least one alkyl aryl sulfonic acid of the formula

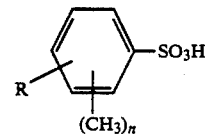

wherein n is one or two and R is an alkyl group having a carbon number in the range from 8 to 18, inclusive, by mixing the acid with a neutralizing agent, the improvement which comprises simultaneously mixing the sulfonic acid with an aqueous solution of the neutralizing agent and with at least one saturated alcohol having a carbon number in the range from 2 to 9, inclusive, under the provisions (i) that the said aqueous solution has a concentration of at least about 10 percent by weight of the neutralizing agent, (ii) that the alcohol is mixed with the acid in such a quantity that the resulting mixture contains between about 5 and 40 parts by weight of alcohol for each 100 parts by weight of neutralized alkyl aryl sulfonate, and (iii) that the aqueous neutralizing agent and alcohol are mixed with the acid in such a quantity that the resulting mixture contains at least about 53 percent by weight of neutralized alkyl aryl sulfonate.

2. The process of claim 1, wherein the aqueous solution has a concentration of at least about 20 percent by weight of the neutralizing agent.

3. The process of claim 2, wherein the alcohol is mixed with the acid in such a quantity that the resulting mixture contains between about 10 and 30 parts by weight of alcohol for each 100 parts by weight of neutralizing alkyl aryl sulfonate.

4. The process of claim 3, wherein the saturated alcohol has a carbon number in the range from 3 to 9, inclusive.

5. The process of claim 4, wherein the resulting mixture is blended with up to 100 parts by weight, for each 100 parts by weight of neutralized alkyl aryl sulfonate, of a cosurfactant selected from the group consisting of alcohol ethoxysulfates, alcohol ethoxylates, alcohol ethoxyacetates, alcohol ethoxysulfonates, alpha-olefin sulfonates, and mixtures thereof.

6. The process of claim 5, wherein the cosurfactant has an average molecular weight in the range from 300 to 750.

7. The process of claim 4, wherein the alkyl aryl sulfonic acid is an alkyl xylene sulfonic acid.

8. The process of claim 7, wherein the neutralizing agent is an alkali metal hydroxide.

9. The process of claim 8, wherein the neutralizing agent is sodium hydroxide.

10. A process for neutralizing at least one alkyl aryl sulfonic acid of the formula

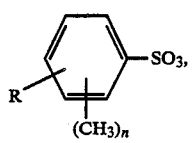

to prepare an alkyl aryl sulfonate concentrate of low viscosity, which comprises steps for (a) mixing at least one saturated alcohol having a carbon number in the range from 2 to 9, inclusive, with an aqueous solution containing at least 10 percent by weight of a neutralizing agent, and (b) mixing the resulting mixture from step (a) with the alkyl aryl sulfonic acid, under the provision that the aqueous solution of neutralizing agent, the alcohol, and the alkyl aryl sulfonic acid are mixed in such relative quantities that the mixture resulting from step (b) contains at least about 53 percent by weight of neutralized alkyl xylene sulfonate and contains between about 5 and 40 parts by weight of alcohol for each 100 parts by weight of neutralized alkyl xylene sulfonate.

11. The process of claim 10, wherein the aqueous solution has a concentration of at least about 20 percent by weight of the neutralizing agent.

12. The process of claim 11, wherein the alcohol is mixed with the acid in such a quantity that the resulting mixture contains between about 10 and 30 parts by weight of alcohol for each 100 parts by weight of neutralized alkyl aryl sulfonate.

13. The process of claim 12, wherein the saturated alcohol has a carbon number in the range from 3 to 9, inclusive.

14. The process of claim 11, wherein the alcohol is mixed with the acid in such a quantity that the resulting mixture contains between about 10 and 30 parts by weight of alcohol for each 100 parts by weight of neutralized alkyl aryl sulfonate.

15. The process of claim 14, wherein the resulting neutralized mixture is blended with up to 100 parts by weight, for each 100 parts by weight of neutralized alkyl aryl sulfonates, of a cosurfactant selected from the group consisting of alcohol ethoxysulfates, alcohol ethoxylates, alcohol ethoxyacetates, alcohol ethoxysulfonates, alpha-olefin sulfonates, and mixture thereof.

16. The process of claim 15, wherein the cosurfactant has an average molecular weight in the range from 300 to 750.

17. The process of claim 16, wherein the alkyl aryl sulfonic acid is an alkyl xylene sulfonic acid.

18. The process of claim 17, wherein the neutralizing agent is an alkali metal hydroxide.

19. The process of claim 18, wherein the neutralizing agent is sodium hydroxide.

20. The process of claim 14, wherein the cosurfactant is one or more alpha-olefin sulfonates.

* * * * *